(12) United States Patent
Blaschke

(10) Patent No.: US 9,164,059 B2
(45) Date of Patent: Oct. 20, 2015

(54) ION MOBILITY SPECTROMETER WITH DEVICE FOR GENERATING AMMONIA GAS

(71) Applicant: Bruker Daltonik GmbH, Bremen (DE)

(72) Inventor: Michael Blaschke, Metzingen (DE)

(*) Notice: Subject to any disclaimer, the term of this patent is extended or adjusted under 35 U.S.C. 154(b) by 0 days.

(21) Appl. No.: 14/260,493

(22) Filed: Apr. 24, 2014

(65) Prior Publication Data

US 2014/0319332 A1    Oct. 30, 2014

(30) Foreign Application Priority Data

Apr. 24, 2013   (EP) ..................... 13002168

(51) Int. Cl.
*H01J 49/26* (2006.01)
*G01N 27/62* (2006.01)
*G01N 33/00* (2006.01)

(52) U.S. Cl.
CPC .......... *G01N 27/622* (2013.01); *G01N 33/0013* (2013.01)

(58) Field of Classification Search
USPC ................... 250/281, 282, 283, 288
See application file for complete search history.

(56) References Cited

U.S. PATENT DOCUMENTS

| 2002/0088936 | A1 | 7/2002 | Breach et al. |
| 2006/0154414 | A1* | 7/2006 | Lin ............................ 438/222 |
| 2009/0166531 | A1 | 7/2009 | Reda |
| 2009/0255351 | A1 | 10/2009 | Stearns et al. |
| 2011/0240838 | A1 | 10/2011 | Debono et al. |

OTHER PUBLICATIONS

Bridgwood, Katy L., et al., Magnesium Nitride, E-EROS Encyclopedia of Reagents for Organic Synthesis, Mar. 15, 2011, page 1.

* cited by examiner

*Primary Examiner* — Nicole Ippolito
(74) *Attorney, Agent, or Firm* — ROBIC, LLP

(57) ABSTRACT

The present invention relates to ion mobility spectrometry, in particular to methods and devices for generating and delivering of ammonia gas as dopant into the ionization region of an ion mobility spectrometer. It provides an ion mobility spectrometer (IMS) with an ion source and device for generating ammonia gas, wherein the device comprises a dopant reservoir filled with alkali metal nitride or alkaline earth metal nitride, preferably lithium nitride and/or magnesium nitride, said reservoir being fluidly coupled to the ion source and to a water reservoir.

15 Claims, 6 Drawing Sheets

ION MOBILITY SPECTROMETER WITH DEVICE FOR GENERATING AMMONIA GAS

BACKGROUND OF THE INVENTION

1. Field of the Invention

This invention relates to ion mobility spectrometry, in particular to methods and devices for generating and delivering of ammonia gas as dopant into the ionization region of an ion mobility spectrometer.

2. Description of the Related Art

Ion mobility spectrometry is based on characterizing chemical substances by the gas-phase mobility of their ionic species under the influence of an electric field. It has been known as an analytical technique since the late 1960s and early 1970s. Ion mobility spectrometers (IMS) operated at ambient pressure are highly sensitive for detecting substances at low concentrations in ambient air and from vaporized samples and have been successfully utilized for the detection of environmental pollutants, explosives and illicit drugs in the civil sector as well as for the detection of chemical warfare agents (CWAs) in the military sector.

The drift-type IMS are most commonly used in commercial instruments and are based on following principles: a gas sample or vapor from a heated sample is introduced into an ionization region to form ions of the gas-phase substances. The ions are introduced into a drift region in a pulsed manner and migrate under the influence of a homogeneous static electric field through a drift tube, normally against a counter flow of dry carrier gas. An ion detector provided at the end of the drift tube is used to measure the drift times taken by the ionic species to pass through the drift tube. The ion mobility of the ionic species can be calculated from the measured drift times, length of the drift tube and the electric field strength in the drift tube. There are other types of IMS operated at ambient pressure, for example Differential Mobility Spectrometry (DMS, also known as Field Asymmetric Ion Mobility Spectrometry, FAIMS) and the aspiration-type IMS.

The gas-phase substances are introduced by a carrier gas into the ionization region of the IMS and are most commonly ionized by chemical ionization (CI). The carrier gas of an IMS is typically purified air with some parts per million (ppm) of water vapor. Electrons emitted from a radioactive beta emitter, such as $^{63}$Ni, generate positive nitrogen ions by electron impact ionization and negative oxygen ions by electron attachment of thermalized electrons. The nitrogen and oxygen ions further react with water molecules present as vapor in the carrier gas to generate positive $(H^+(H_2O)_n)$ or negative water cluster ions $(O_2^-(H_2O)_n)$, respectively. These secondary reactant ions react with gas-phase substances by protonation forming positive product ions, or by adduct formation forming negative product ions. The primary oxygen ions may also react with gas-phase substances by de-protonation, electron transfer or adduct formation forming negative product ions. The electrons generating primary reactant ions can be provided by radioactive as well as by non-radioactive electron sources, such as those using corona discharges, electron beam generators and/or UV/X-Ray lamps.

It is well known in ion mobility spectrometry that an additional gas-phase reagent (dopant) can be provided in the ionization region together with the gas-phase substances to be analyzed in order to improve sensitivity and selectivity to substances of interest (target substances), or to improve the rejection of interfering substances (i.e., those substances which may otherwise give rise to a signal interfering with the ion signal of the target substance(s)). Dopants modify the composition of the reactant ions such that the composition of the product ions is changed to improve the sensitivity and selectivity of the IMS. In the positive mode (i.e., when positive product ions are measured in the IMS), it is necessary that the ionic species of the dopant (including molecular ions and adduct ions with water) have a proton affinity less than that of the substance of interest and higher than that of other interfering substances such that product ions of substances of interest are preferably generated compared to interfering substances. Furthermore, since the proton affinity of the substance of interest is greater than that of the dopant ions, the gas-phase substances of interest can almost completely react with the ionic species of the dopant to effectively form product ions of the substance of interest.

Furthermore, dopants typically shift peak positions of product ions in the mobility spectrum by formation of adducts such that the signal peaks of substances of interest can be separated from each other or from signal peaks of interfering substances and can thus be identified even in the presence of interfering substances. If no dopant is added, the signal peaks of substances of interest can be hardly distinguished due to peak overlap.

Dopant delivery devices for use in IMS commonly comprise a sealed dopant reservoir with a permeation capability containing a dopant material, with the dopant reservoir being incorporated in the gas circulating system comprising a pump and means for drying and cleaning the recirculating gases. The commonly used dopants for detecting drugs in the positive mode include acetone and preferably ammonia. Dopants usually used for detecting explosives in the negative mode are halogenated compounds, such as chloride. For CWAs, ammonia is preferably used as dopant in the positive mode whereas in the negative mode usually no dopant is used because many target substances contain halogens.

Some IMS have been known to deliver ammonia gas as dopant by evaporating liquid anhydrous ammonia. While operating the IMS with dopant delivery, a dopant reservoir filled with liquid ammonia facilitates a controlled release of ammonia gas into the carrier gas after permeation through a membrane located between the liquid ammonia and the gas circulating system of the IMS. However, the use of liquid ammonia creates a number of difficulties. Ammonia is considered a highly toxic material and, according to the International Air Transport Association, may not be transported on passenger aircraft. Prior to use in the IMS, the dopant reservoir is typically hermetically sealed and frozen. Liquid ammonia must be pressurized to maintain a liquid form at room temperature. The vapor pressure of ammonia at room temperature is already about 8,600 hPa and a dopant reservoir must therefore be able to withstand a pressure of approximately 14,000 hPa without leaking. Because such a dopant reservoir is highly pressurized while operating the IMS with dopant delivery, the size of the dopant reservoir and thus its operating time is limited and the transportation of the IMS may be further restricted.

U.S. Patent Publication 2002/0088936 A1 (by Breach et al.) describes an IMS with a gas circulating system comprising means for drying and/or cleaning the circulating gas and a dopant source, wherein said means and the dopant source are physically combined, obviating the need for a separate dopant source. The dopant source material may be combined with the material for drying and/or cleaning the circulating gas, for example a molecular sieve material filled with adsorbed ammonium gas.

U.S. Patent Publication 2009/0255351 A1 (by Stearns et al.) describes a device for delivering ammonia gas for use in an IMS without having a reservoir containing ammonia. The delivery device includes an ammonium solid (e.g., ammonium carbamate ($NH_2COONH_4$) or ammonium carbonate (($NH_4)_2CO_3$), that will, upon the introduction of heat, release ammonia gas for delivery into the IMS. The volumetric flow rate of the ammonia gas is controlled by the use of capillary tubes as the exiting pathway, where the flow rate is determined by the cross sectional area and length of the capillary tube. Delivery of the ammonia is aided by use of a frit or screen to permit only gas to exit.

U.S. Patent Publication 2009/0166531 A1 (by Reda) describes a device for delivering ammonia gas for use in an IMS. The device includes a gas permeable tube containing an ammonia compound and is sized to be inserted into a space within the IMS. The device is configured to activate the ammonia compound to decompose into an ammonia gas that does not include water vapor, and emit the ammonia gas into the IMS. In the exemplary embodiment, the ammonia compound is ammonium carbamate ($NH_2COONH_4$) which decomposes into ammonia gas $NH_3$ and carbon dioxide $CO_2$ without producing any water vapor.

U.S. Patent Publication 2011/0240838 A1 (by Debono et al.) describes a device for delivering ammonia gas for use in an IMS comprising a permeation tube, ammonium sulfate disposed within the permeation tube in solid form, and a heating device configured to heat the permeation tube so as to create ammonia gas.

It is an ongoing aim to provide an IMS with a dopant delivery device for generating ammonia gas wherein the device has low power consumption and delivers ammonia gas at a preferably constant flow rate over a wide range of operating temperatures. It is a further aim that the dopant delivery device should have an operating time not further limiting the operating time of the IMS.

SUMMARY OF THE INVENTION

In a first aspect, the invention provides an ion mobility spectrometer (IMS) with an ion source and device for generating ammonia gas, wherein the device comprises a dopant reservoir filled with alkali metal nitride or alkaline earth metal nitride, said reservoir being fluidly coupled to the ion source and to a water reservoir. The IMS may comprise a reservoir with an additional dopant material other than alkali metal nitride or alkaline earth metal nitride suitable for generating ammonia gas at temperature below −10° C.

The dopant reservoir is preferably filled with one of lithium nitride ($Li_3N$) and magnesium nitride ($Mg_3N_2$). Sodium and potassium nitrides are likewise possible. Lithium nitride and magnesium nitride exothermically react with water to ammonia gas and respective hydroxides:

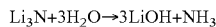

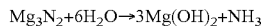

Lithium nitride (CAS No. 26134-62-3) is highly flammable, reacts violently with water and causes burns. However, lithium hydroxide binds carbon dioxide $CO_2$ which has a strong electron affinity and therefore disturbs the generation of negative product ions. A high concentration of carbon dioxide in the ionization region can cause a so-called "poisoning" of the IMS operated in the negative mode. Magnesium nitride (CAS No. 12057-71-5) is less basic than lithium nitride. It is not toxic and only irritant to skin, eye and respiratory ducts. Both lithium nitride and magnesium are listed under hazard class 4.3 (dangerous as wet material) and meet the safety requirements of a civil commercial instrument.

The dopant reservoir can be integrated into the gas circulating system of the IMS ion mobility spectrometer wherein the gas and/or the inner surface of the gas circulating system can be the water reservoir needed for forming the ammonia gas. Preferably, the water reservoir comprises a container with water absorbing material, such as a moist molecular sieve. Most preferably, the dopant reservoir comprises dopant material (alkali metal nitride or alkaline earth metal nitride) and a moist molecular sieve, wherein the container can be a tube closed with mineral fiber felt at both ends and fluidly coupled to the circulating system of the IMS. The moist molecular sieve in the container preferably has water content between 10 and 40 percent at the beginning of operation. The container typically has a volume between 0.1 and 3 ml and is filled with 5 to 100 mg of the dopant material. However, the dopant reservoir can also comprise dopant material and a volume with liquid water wherein the dopant material and the water volume are separated by a membrane that is permeable for water vapor. The water for the chemical reaction may also at least partly originate from the ambient air as humidity migrates through sealings and tubings and is in addition introduced into the system by the sample gas flow.

In a second aspect, the invention provides a method for operating an ion mobility spectrometer, comprising the steps: (a) providing water vapor or liquid water to a dopant reservoir filled with alkali metal nitride or alkaline earth metal nitride to generate the ammonia gas; (b) transporting the ammonia gas and a gaseous sample into an ionization region of the ion mobility spectrometer; and (c) measuring an ion mobility spectrum of ions generated in the ionization region.

The dopant reservoir is preferably filled with lithium nitride ($Li_3N$) and/or magnesium nitride ($Mg_3N_2$). The ammonia gas is generated by exothermic reactions of the alkali metal nitride or alkaline earth metal nitride with water. The concentration of the water vapor at the dopant material is in the range of 0.5 to 100 ppm, preferably in the range of 1 to 20 ppm, most preferably at 10 ppm. The ammonia gas can be transported by diffusion or driven convection into an ionization region.

According to the present invention, exothermic reactions are utilized to generate the ammonia gas, i.e., that they run under stoichiometric ratio even at low temperature and therefore ensure a sufficiently constant flow rate of ammonia gas over a wide temperature range. In the prior art, ammonia gas is generated by decomposing ammonium compounds and by the diffusion of ammonium vapor through a permeable membrane. Both processes strongly dependent on the operating temperature of the IMS and can therefore not provide constant flow rate of ammonium gas over a wide range without further efforts to control the temperature of the dopant delivery device. The delivery of ammonia gas according to the present invention does not consume power of the IMS whereas the decomposition of ammonium compounds as described above in principle relies on heating a dopant material to release ammonia gas. Ammonium sulfate does not decompose below 235° C.; ammonium carbamate decomposes completely at temperatures of 60° C. and upwards. The decomposition of ammonium carbamate has the additional disadvantage in that carbon dioxide $CO_2$ is released which may compromise the IMS operated in the negative mode.

DETAILED DESCRIPTION

Embodiments of the present invention will be described below, by way of example only, with reference to the drawings. It should be noted that the figures are schematic and not drawn to scale. Relative dimensions and proportions of parts of the figures may be shown exaggerated or reduced in size, for the sake of clarity and convenience. In the figures, the same reference signs are used to refer to corresponding or similar elements in modified and different embodiments.

Figure 1:
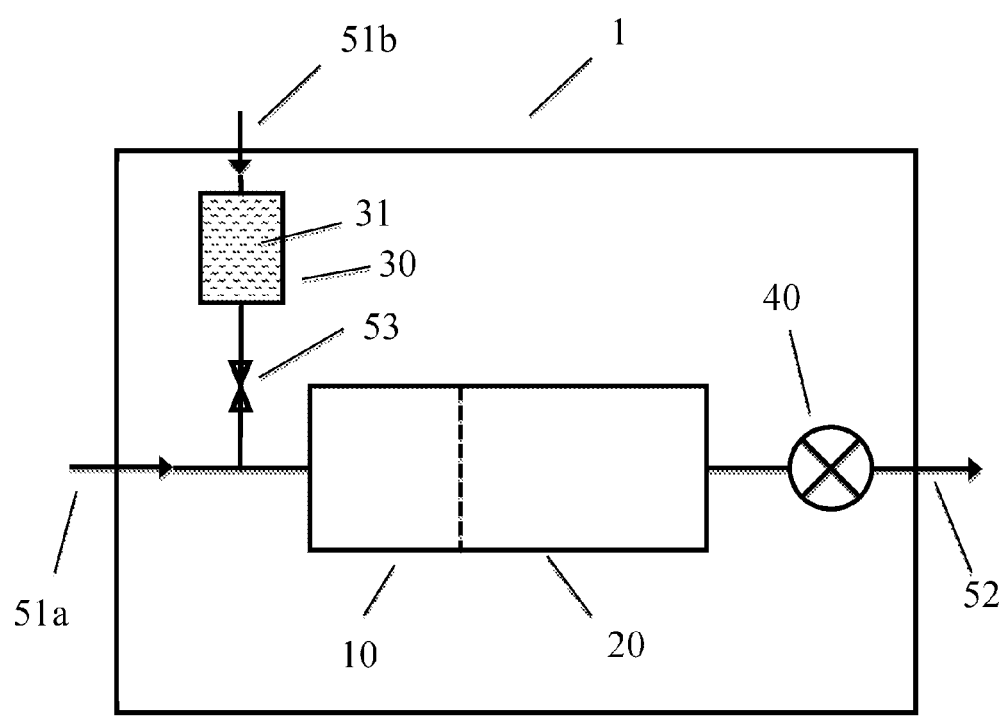
FIG. 1 shows an IMS with a direct sample inlet and a gas circulating system comprising a dopant reservoir.

FIG. 1 shows an ion mobility spectrometer 1 that comprises an ionization source 10, a mobility analyzer 20, a dopant reservoir 30 and a gas pump 40. The ion source 10 is operated at atmospheric pressure generating ions by chemical ionization utilizing a radioactive beta emitter ($^{63}$Nickel), an electrical discharge or a non-radioactive electron source as described for example in WO 93/11554 A1 or EP 1070960 A2. The ion mobility analyzer 20 is preferably a commonly used drift-type mobility analyzer, but may also be a filter-type mobility analyzer (DMS=differential mobility spectrometry) or an aspiration-type mobility analyzer.

When pump 40 is operating, an air sample (or more generally a gas sample to be analyzed) is drawn into the ion source 10 at a first inlet 51a from surrounding. The ion mobility spectrometer 1 comprises an additional inlet 51b. If valve 53 is opened, air from outside is also drawn into dopant reservoir 30. The dopant reservoir 30 is filled with alkali metal nitride or alkaline earth metal nitride 31, preferably with lithium nitride ($Li_3N$) and most preferably with magnesium nitride ($Mg_3N_2$). The water vapor of the humid air drawn in at inlet 51b reacts exothermically with the nitride containing material 31 of the dopant reservoir 30 to generate ammonia gas and respective hydroxides. The air volume drawn in at inlets 51a and 51b is exhausted at the outlet 52. The delivery of ammonia gas from dopant reservoir 30 into the ion source 10 can be controlled by opening and closing of valve 53.

Since the reactions inside the dopant reservoir 30 are exothermic, they run under stoichiometric ratio even at low temperature and therefore ensure a stable flow rate of ammonia gas over a wide temperature range. The water content of the air drawn into the dopant reservoir 30 is preferably in the range of 0.5 to 100 ppm, preferably in the range of 1 to 20 ppm, most preferably at 10 ppm. The ammonia enriched gas generated in the dopant reservoir 30 is introduced into the ion source 10 together with the air sample drawn in at inlet 51a. The ammonia gas acts as dopant particularly for the positive ion mode and modifies the composition of the reactant ions in the ion source 10 such that the composition of the product ions (analyte ions) is changed to improve the sensitivity and selectivity of the ion mobility spectrometer 1. Ions generated in the ion source 10 are guided into the ion mobility analyzer by a gas flow and/or by electrical DC fields.

Figure 2:
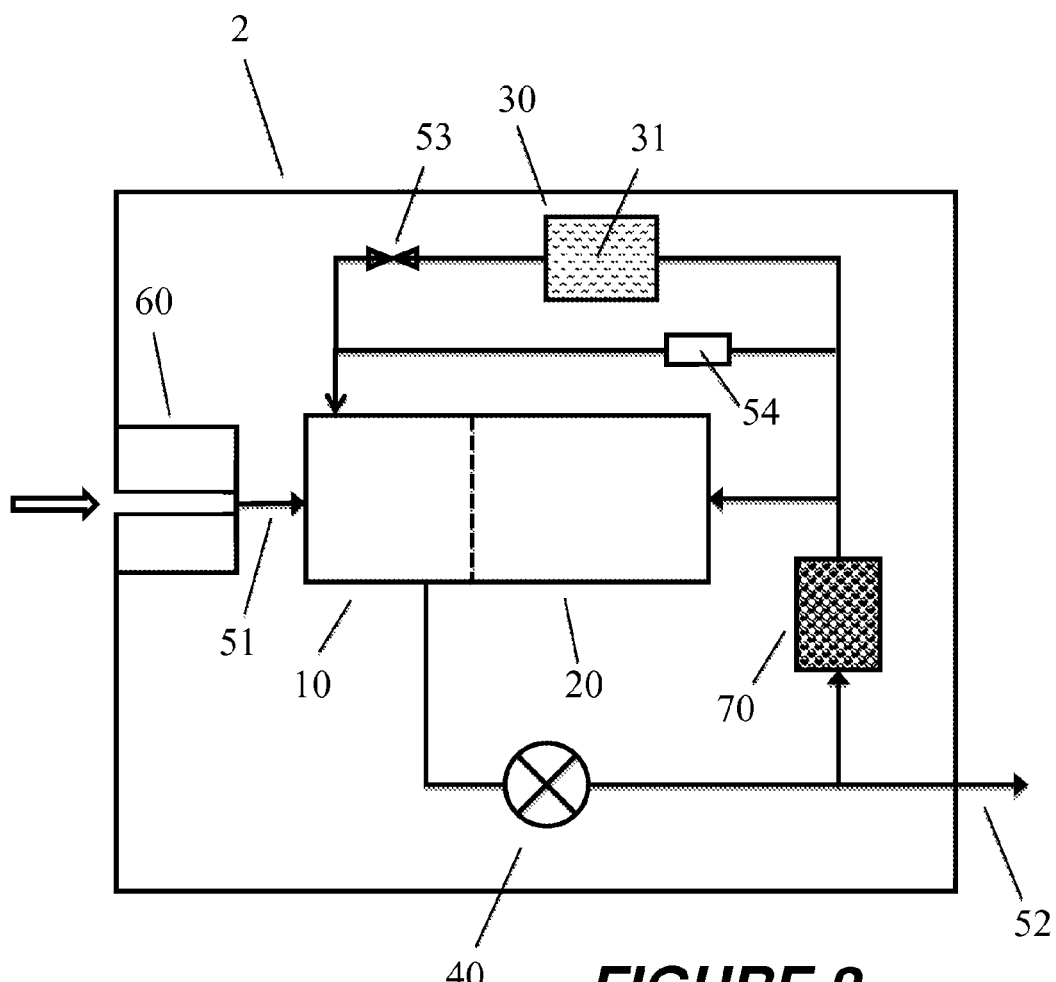
FIG. 2 shows an IMS with a direct sample inlet and a gas circulating system comprising a dopant reservoir which is positioned in a switchable sideline of the gas circulating system.

FIG. 2 shows an ion mobility spectrometer 2 that comprises an ionization source 10, a mobility analyzer 20 (preferably a drift-type mobility analyzer), a dopant reservoir 30, a gas pump 40, a desorbing unit 60 and a filter 70.

Ion mobility spectrometers are widely-used to detect target substances in the civil sector, such as explosives and illicit drugs. The target substances are usually detected via their vapors. The detection of modern explosives and drugs, in particular, is hampered by the fact that these target substances have a very low vapor pressure and are often enclosed in transport containers. In most cases, direct detection of these target substances in the ambient air is therefore only possible by collecting a large sample volume with subsequent enrichment. However, the surfaces of the baggage, the transport containers and the clothes and skin of the persons doing the packing are usually contaminated with minimal traces of the substances, which are present as condensations from vapors on the surface itself or as particles adhering to the surface of the containers. They have vapor pressures too low to be directly detectable in the ambient air. The surfaces to be investigated are therefore wiped with a sampler, causing condensed substances and particles carrying the substances to be removed from the surface and to adhere to the sampler. Currently, paper, woven fabrics or felt are used as samplers, for instance. After wiping the surface to be investigated, the sampler is transferred into the desorption unit 60 of a ion mobility spectrometer 2, where it is heated in order to increase the vapor pressures of the target substances which are sufficient for detection. The desorbing unit 60 is fluidly coupled to the ion source 10 by inlet 51.

The ion mobility spectrometer 2 comprises an internal gas circulating system. When pump 40 is operating and intake of sample gas from the desorbing unit 60 is disabled by closing inlet 51, gas is pumped from the ion source 10 through the filter 70 into the mobility analyzer 20 and back into the ion source 10 via gas restriction 54 and optionally via the dopant reservoir 30. A flow of filtered gas is often used in drift-type mobility analyzers in which ions drift in a counter flowing gas to keep neutral substances away from mobility analyzer where ions are analyzed according to their ion mobility. Without a counter-flowing gas, neutral substances can diffuse into the drift region of the drift-type mobility analyzer and react with drifting ions such that the drift time of ions is affected and their ion mobility is determined inaccurately. When the desorbing unit 60 is loaded with a sampler and heats the sampler, inlet 51 is opened and sample gas is drawn into the ion source 10. The amount of gas drawn into the ion mobility analyzer 2 is exhausted at outlet 52 positioned between the pump 40 and filter 70.

The circulating gas drawn out from the ion source 10 is continuously cleaned of substances and freed of moisture in the filter 70. The filter 70 is most commonly an activated charcoal combined with a molecular sieve. The moisture in the ion source 10 is preferably held constant at a level of less than 100 ppm, preferably around 10 ppm. Constant moisture in the ion source 10 and the mobility analyzer is helpful to establish stable conditions for the ionization process and to enable accurate measurement of the mobility, respectively.

The dopant reservoir 30 is filled with alkali metal nitride or alkaline earth metal nitride 31, preferably with lithium nitride ($Li_3N$) and most preferably with magnesium nitride ($Mg_3N_2$). When valve 53 is opened, part of the circulating gas passes through the dopant reservoir 30 and is re-fed into the ion source 10. The water vapor of the circulating gas reacts with the nitrides containing material 31 of the dopant reservoir 30 and generates ammonia gas which is introduced with the circulating gas into the ion source 10.

Figure 3:
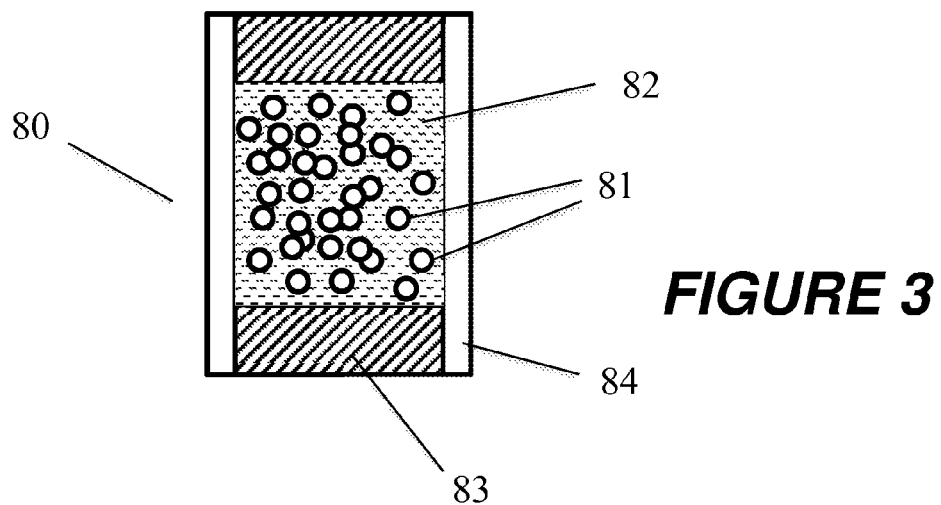
FIG. 3 shows a dopant reservoir integrating water and materials containing nitride.

FIG. 3 shows a dopant reservoir 80 comprising moist molecular sieve 81, preferably a 13X molecular sieve, and nitride powder 82, preferably magnesium nitride ($Mg_3N_2$). The molecular sieve 81 and the nitride powder 82 are placed in a tube 84 which is preferably terminated by mineral fiber felt 83 at both ends. The dopant reservoir 80 can be placed in a common filter cartridge with standardized fittings and be fluidly coupled to the ion source of an ion mobility spectrometer.

The dopant reservoir 80 typically has a volume between 0.1 and 3 ml and is filled with 5 to 100 mg of the nitride powder 82. The moist molecular sieve 81 is a water reservoir fluidly coupled to the nitride powder 82 and provides the water vapor needed for the reaction with the nitride powder 82. At the beginning of operating the ion mobility spectrometer, the water content of the molecular sieve 81 is preferably between 10 and 40 percent. An estimation shows that an ion mobility spectrometer can be operated in a dopant mode for 250 hours at an ammonia level of 2 ppm with a dopant reservoir 80 containing about 20 mg magnesium nitride and 300 mg moist molecular sieve when the dopant reservoir 80 is flushed at a low rate of about 20l/h.

Figure 4:
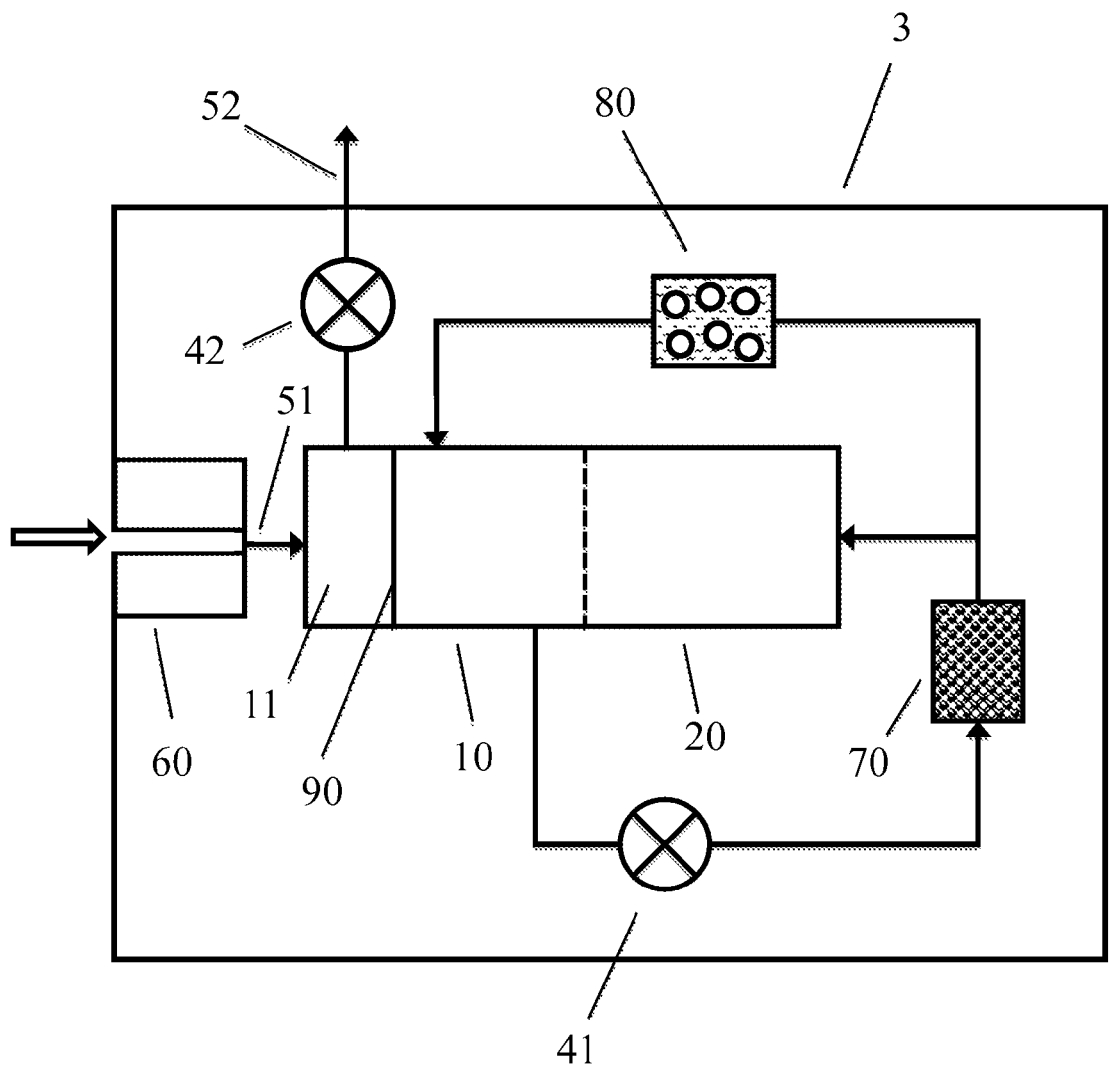
FIG. 4 shows an IMS with a membrane inlet and a closed gas circulating system with the integrated water and dopant reservoir.

FIG. 4 shows an ion mobility spectrometer 3 that comprises an ionization source 10, a mobility analyzer 20 (preferably a drift-type mobility analyzer), a dopant reservoir 80, a first gas pump 41, a second gas pump 42, a desorbing unit 60 and a filter 70.

The desorbing unit 60 is fluidly coupled to chamber 11 which is separated from the ion source 10 by a semi-permeable membrane made of polysiloxane, for instance. When the desorbing unit 60 is loaded with a sampler and the sampler is heated in there, sample gas is drawn from the desorbing unit 60 into the chamber 11 by pump 42. The semi-permeable membrane 90 is thus flushed from outside with sample gas and from inside with gas of a closed gas circulating system. The target substances enter the ion source 10 via the semi-permeable membrane 90. The semi-permeable membrane 90 is commonly heated in order to reduce memory effects. The sample gas is exhausted at outlet 52.

In the closed gas circulating system, gas is pumped from the ion source 10 through the filter 70 into the mobility analyzer 20 and back into the ion source 10 via the dopant reservoir 80. The dopant reservoir 80 comprises a moist molecular sieve and nitride containing material, preferably magnesium nitride ($Mg_3N_2$). The ammonia gas generated in the dopant reservoir 80 is continuously carried into the ion source 10 by gas flowing through the dopant reservoir 80 (convective transport). The circulated gas is continuously cleaned from target substances and freed of moisture in the filter 70. The filter 70 is most commonly an activated charcoal combined with a molecular sieve.

Figure 5:
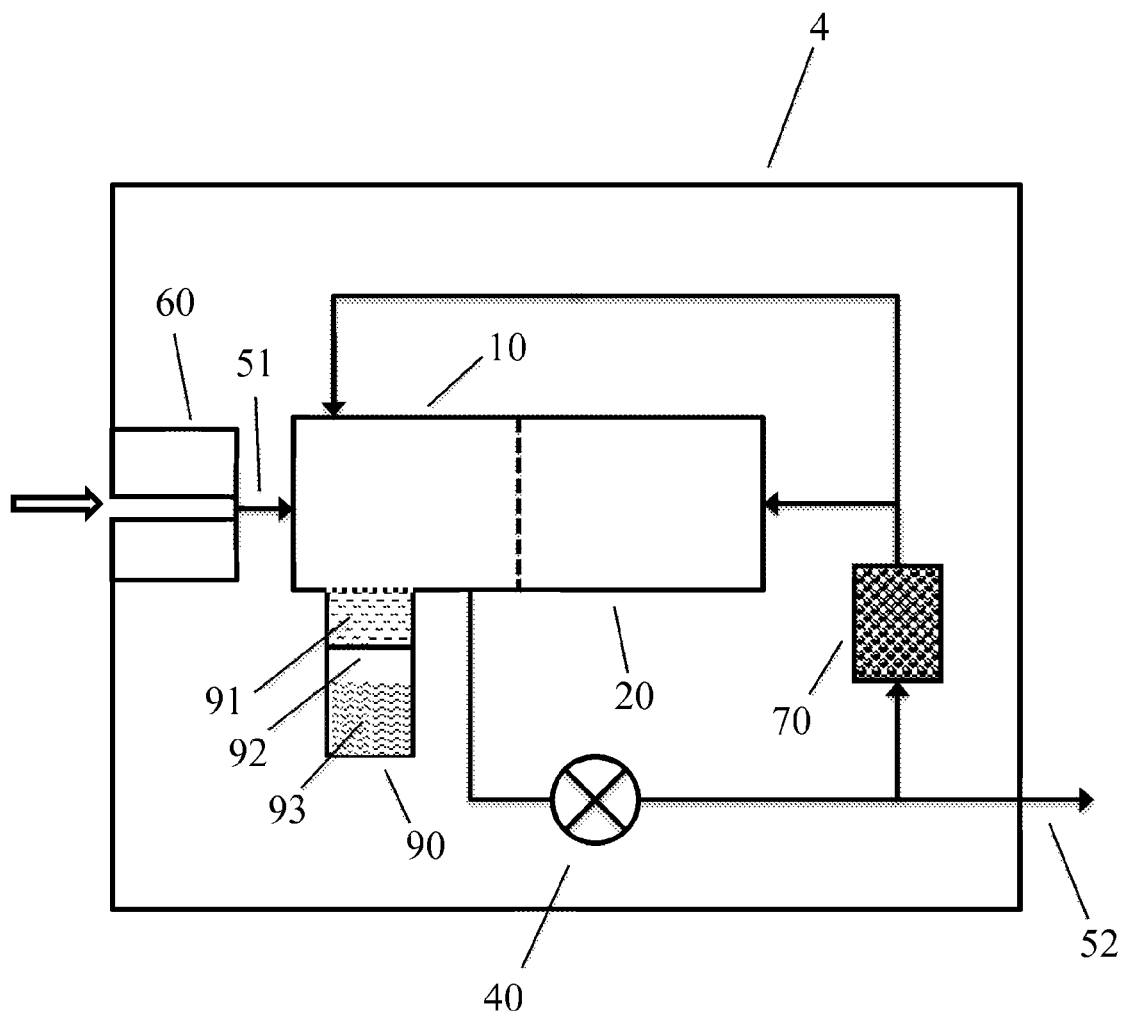
FIG. 5 shows an IMS with an integrated water and dopant reservoir directly connected to the ion source wherein a volume of water is separated from the dopant reservoir by a permeable membrane.

FIG. 5 shows an ion mobility spectrometer 4 that comprises an ionization source 10, a mobility analyzer 20 (preferably a drift-type mobility analyzer), a gas pump 40, a desorbing unit 60, a filter 70 and a dopant reservoir 90.

The desorbing unit 60 is fluidly coupled to the ion source 10 by inlet 51. When pump 40 is operating and intake of sample gas from the desorbing unit 60 is disabled by closing inlet 51, gas is pumped from the ion source 10 through the filter 70 into the mobility analyzer 20 and back into the ion source 10. When the desorbing unit 60 is loaded with a sampler and the sampler is heated, inlet 51 is opened and sample gas is drawn into the ion source 10. The amount of gas drawn into the ion mobility analyzer 4 via inlet 51 is exhausted at outlet 52 positioned between the pump 40 and filter 70. The circulating gas drawn out from the ion source 10 is continuously cleaned of substances and freed of moisture in the filter 70.

The dopant reservoir 90 is directly attached to the ion source 10. It comprises a nitride containing material 91 which is separated from a water containing volume 93 by a vapor permeable membrane 92. The water containing volume 93 may be filled with a moist molecular sieve and/or with liquid water. Water vapor from water containing volume 93 permeates the membrane 92 and reaches the nitride containing material 91. The ammonia gas generated in the reaction of the water vapor and the nitride(s) is supplied to the ion source 10 by diffusion.

Figure 6:
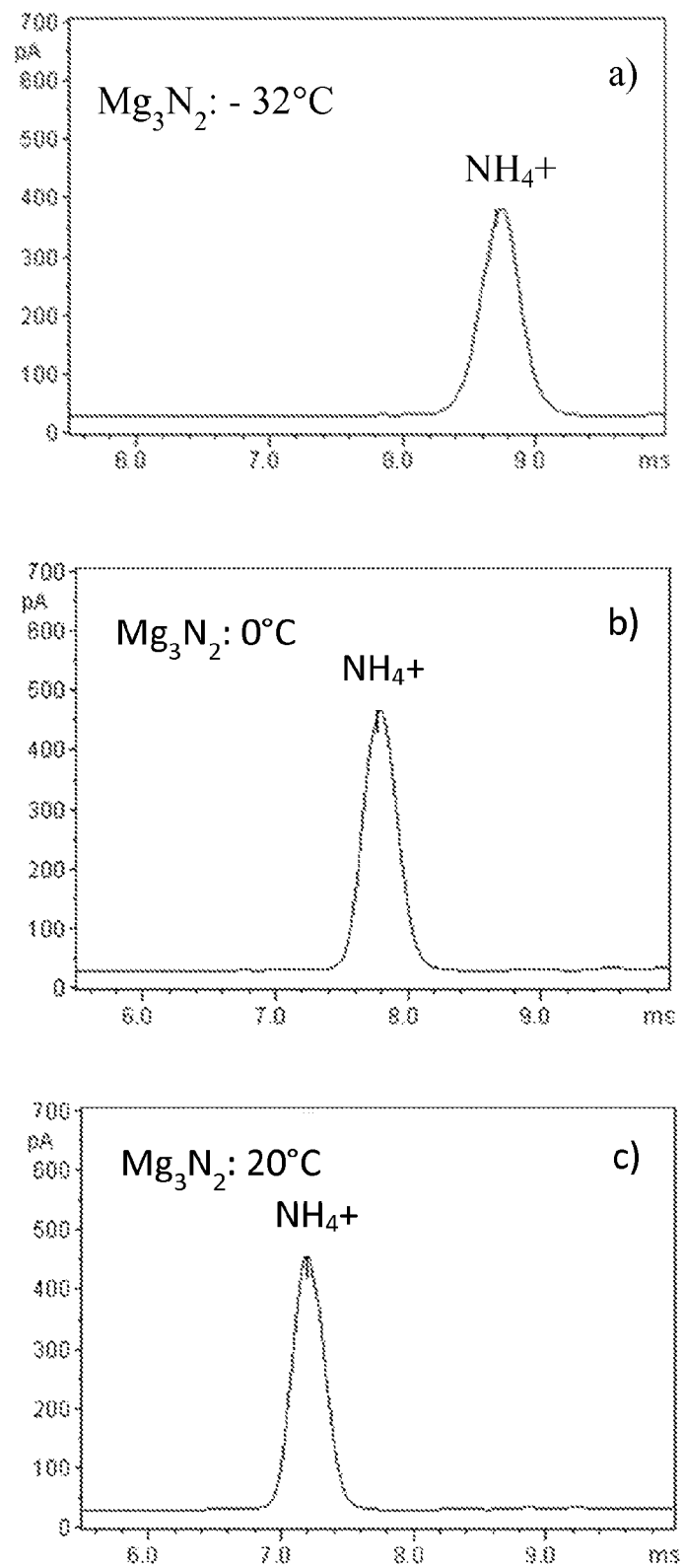
FIG. 6 shows a series of ion mobility spectra acquired with a drift type instrument using magnesium nitride as dopant material at different temperatures measured in positive mode.
Figure 7:
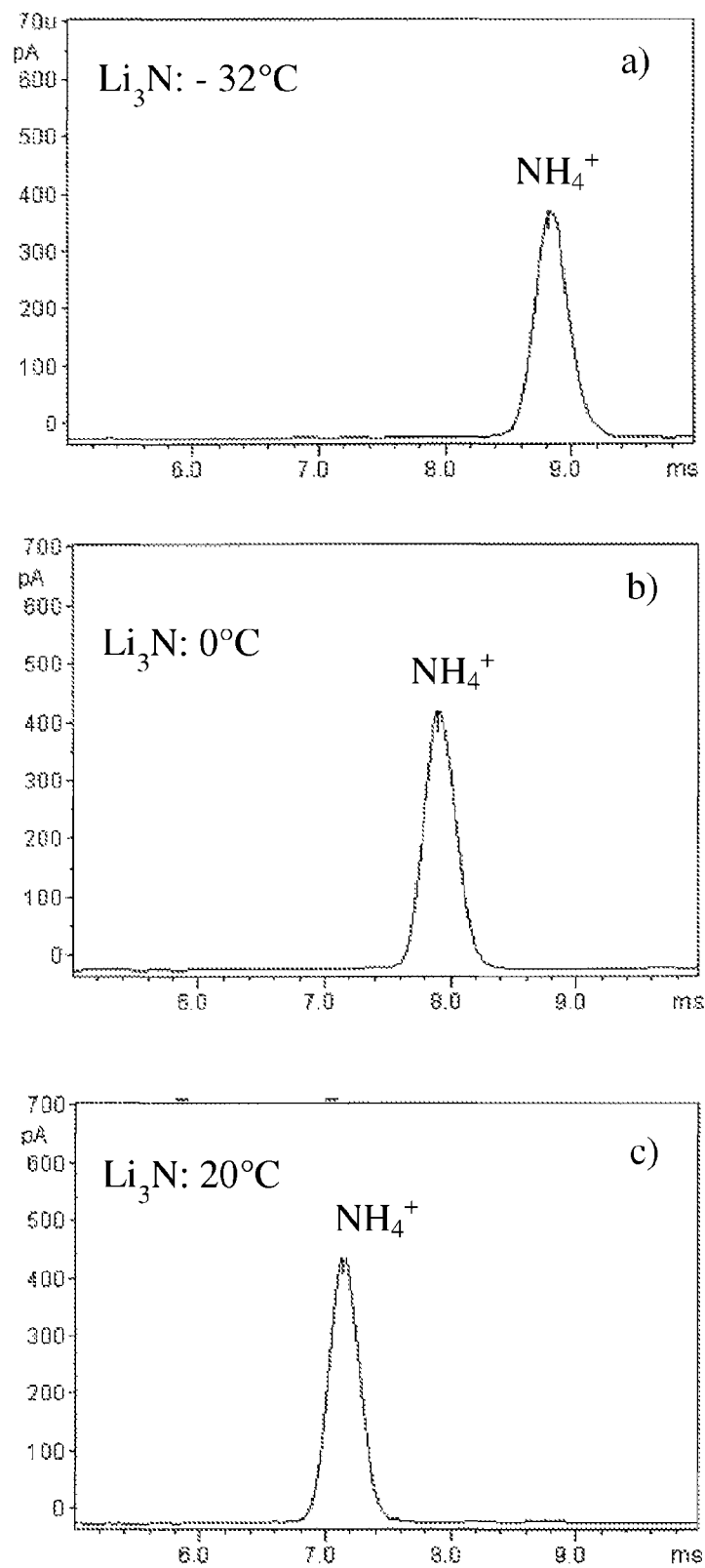
FIG. 7 shows a series of ion mobility spectra acquired with a drift type instrument using lithium nitride as dopant material at different temperatures measured in positive mode.

FIGS. 6 and 7 show ion mobility spectra of the ammonia ion ($NH_4^+$) measured with ion mobility analyzer of FIG. 4 using a drift-type mobility analyzer. The ion currents are measured in time by a Faraday cup at the end of the drift region to which the ions are introduced in a pulsed manner. All ion mobility spectra of FIGS. 6 and 7 are measured in positive ion mode. However, it is to be understood that, in principle, measurements in the negative ion mode are also conceivable. The ion mobility spectra of FIG. 6 are measured with a dopant reservoir 80 filled with magnesium nitride ($Mg_3N_2$), whereas lithium nitride ($Li_3N$) is used as nitride containing material in FIG. 7.

The ion mobility spectra are acquired at different surrounding temperatures. The ion mobility spectra at −32° C. are acquired after a warm-up time of 30 min. The $NH_4^+$ signals in the mobility spectra shown in FIGS. 6 and 7 have a constant peak area over a wide temperature range, i.e., ammonia gas is provided into the ion source with a constant rate over the temperature range. The $NH_4^+$ signals are shifted on the drift-time axis towards smaller drift times as a general effect when the temperature of the gas inside the drift-type mobility analyzer is increased.

While the invention has been shown and described with reference to a number of embodiments thereof, it will be recognized by those skilled in the art that various changes in form and detail may be made herein without departing from the spirit and scope of the invention as defined by the appended claims.

The invention claimed is:

1. An ion mobility spectrometer having an ion source and a device for generating ammonia gas, characterized in that the device comprises a dopant reservoir filled with at least one of alkali metal nitride and alkaline earth metal nitride, said reservoir being fluidly coupled to the ion source and to a water reservoir.

2. The ion mobility spectrometer according to claim 1, wherein the dopant reservoir is filled with one of lithium nitride ($Li_3N$) and magnesium nitride ($Mg_3N_2$).

3. The ion mobility spectrometer according to claim 1, wherein the dopant reservoir is integrated into a gas circulating system of the ion mobility spectrometer and wherein at least one of the gas and the inner surface of the circulating system are the water reservoir.

4. The ion mobility spectrometer according to claim 1, wherein the water reservoir comprises a container with water absorbing material.

5. The ion mobility spectrometer according to claim 1, wherein the dopant reservoir comprises a container with a moist molecular sieve and dopant material.

6. The ion mobility spectrometer according to claim 5, wherein the container is a tube closed with mineral fiber felt at both ends and fluidly coupled to a circulating system of the ion mobility spectrometer.

7. The ion mobility spectrometer according to claim 5, wherein the molecular sieve has water content between 10 and 40 percent.

8. The ion mobility spectrometer according to claim 5, wherein the container has a volume between 0.1 and 3 ml.

9. The ion mobility spectrometer according to claim 5, wherein the container is filled with 5 to 100 mg of the dopant material.

10. The ion mobility spectrometer according to claim 1, wherein the dopant reservoir comprises a volume with liquid water and dopant material, and wherein the dopant material and the water volume are separated by a membrane that is permeable for water vapor.

11. The ion mobility spectrometer according to claim 1, further comprising a reservoir with a dopant material other than alkali metal nitride or alkaline earth metal nitride suitable for generating ammonia gas at temperature below −10° C.

12. A method for operating an ion mobility spectrometer, comprising the steps:

(a) providing one of water vapor and liquid water to a dopant reservoir filled with alkali metal nitride or alkaline earth metal nitride to generate ammonia gas;

(b) transporting the ammonia gas and a gaseous sample into an ionization region of the ion mobility spectrometer; and (c) measuring an ion mobility spectrum of ions generated in the ionization region.

13. The method according to claim 12, wherein the dopant reservoir is filled with one of lithium nitride (Li3N) and magnesium nitride ($Mg_3N_2$).

14. The method according to claim 12, wherein the ammonia gas is transported by diffusion or by driven convection into the ionization region.

15. The method according to claim 12, wherein the concentration of the water vapor at the dopant material is in the range of 0.5 to 100 ppm.

* * * * *